United States Patent [19]

Behrens et al.

[11] Patent Number: 5,350,874
[45] Date of Patent: Sep. 27, 1994

[54] PROCESS FOR PREPARING DIESTERS OF NAPHTHALENEDICARBOXYLIC ACIDS

[75] Inventors: Paul K. Behrens, Warrenville; Juergen K. Holzhauer, Naperville; Gregory P. Hussmann, Batavia; David L. Sikkenga, Wheaton, all of Ill.

[73] Assignee: Amoco Corporation, Chicago, Ill.

[21] Appl. No.: 981,184

[22] Filed: Nov. 24, 1992

[51] Int. Cl.$^5$ ............................................. C07C 67/08
[52] U.S. Cl. ...................................... 560/80; 560/77; 560/98
[58] Field of Search ...................................... 560/80, 98

[56] References Cited

U.S. PATENT DOCUMENTS 4,003,948  1/1977  Yamashita et al. .................... 560/98

FOREIGN PATENT DOCUMENTS 48-96574  12/1973  Japan .
50-76055   6/1975  Japan .
50-76057   6/1975  Japan .
50-83362   7/1975  Japan .
50-95253   7/1975  Japan .

*Primary Examiner*—José G. Dees
*Assistant Examiner*—Vera C. Clarke
*Attorney, Agent, or Firm*—Thomas E. Nemo; Wallace L. Oliver

[57] ABSTRACT

A continuous process for preparing a dialkylester of a naphthalenedicarboxylic acid comprising passing a liquid phase reaction mixture comprising a low molecular weight alcohol, a naphthalenedicarboxylic acid and a dialkylester of a naphthalenedicarboxylic acid at an elevated temperature through series arranged reaction zones while introducing a naphthalenedicarboxylic acid and a low molecular weight alcohol to an upstream reaction zone, agitating at least one reaction zone, and removing a liquid product mixture comprising the dialkylester of the naphthalenedicarboxylic acid produced by the reaction of the naphthalenedicarboxylic acid with the low molecular weight alcohol from a downstream reaction zone.

19 Claims, 1 Drawing Sheet

PROCESS FOR PREPARING DIESTERS OF NAPHTHALENEDICARBOXYLIC ACIDS

FIELD OF THE INVENTION

This invention relates to a process for preparing a dialkylester of a naphthalenedicarboxylic acid. More particularly, this invention relates to an improved process for preparing a dialkylester of a naphthalenedicarboxylic acid by reacting a naphthalenedicarboxylic acid with a low molecular weight alcohol at an elevated reaction temperature in series arranged reaction zones under conditions which provide for high reaction rates and high conversion of the naphthalenedicarboxylic acid to its diester without excessive formation of side products.

BACKGROUND OF THE INVENTION

The diesters of naphthalenedicarboxylic acids are useful for preparing a variety of polymeric materials such as polyesters and polyamides. One particularly useful diester is dimethyl-2,6-naphthalenedicarboxylate (DM-2,6-NDC). Dimethyl-2,6-naphthalenedicarboxylate, for example, can be condensed with ethylene glycol to form poly(ethylene-2,6-naphthalate) (PEN), a high performance polyester material. Fibers and films made from PEN have considerably improved strength and superior thermal properties relative to, for example, poly(ethyleneterephthalate). For this reason, PEN is an exceptional material for preparing commercial articles such as thin films which can be used in the manufacture of magnetic recording tape and electronic components. Additionally, because of its superior resistance to gas diffusion, and particularly to the diffusion of carbon dioxide, oxygen and water vapor, films made from PEN are useful for manufacturing food containers, especially the so-called "hot fill" food containers. PEN can also be used to prepare high strength fibers useful for the manufacture of, for example, tire cord.

DM-2,6-NDC is most readily prepared by the esterification of 2,6-naphthalenedicarboxylic acid (2,6-NDA) with methanol. The 2,6-NDA is conveniently prepared by the liquid phase, heavy metal catalyzed oxidation of a 2,6-dialkyl- or 2-alkyl-6-acyl-naphthalene compound using molecular oxygen as the source of oxygen for the oxidation reaction. During this oxidation reaction, impurities such as 2-formyl-6-naphthoic acid (FNA), trimellitic acid (TMLA) and, when bromine oxidation promoter is used, various brominated compounds are produced. Although in some instances it would be desirable to use 2,6-NDA directly for the preparation of PEN, however, because of its high melting point (>300° C. with decomposition) and extremely low solubility in ordinary solvents, 2,6-NDA is difficult to purify to acceptable levels by standard purification techniques such as adsorption or recrystallization. These difficulties in purifying 2,6-NDA are partially overcome by converting 2,6-NDA to its dimethyl ester, DM-2,6-NDC. DM-2,6-NDC can be distilled and it can be recrystallized from solvents such as methanol or from one or more aromatic solvents.

For a large-scale commercial process for preparing diesters of naphthalenedicarboxylic acids, such as dimethyl-2,6-naphthalenedicarboxylate, it would be highly advantageous to produce the diester in a continuous manner at high reaction rates, using a minimum amount of alcohol component for the esterification reaction, as well as using the least expensive reactor equipment. There is a continuing need for improved processes for esterifying naphthalenedicarboxylic acids, such as 2,6-naphthalenedicarboxylic acid. The present invention provides such an improved process.

Methods for preparing diesters of naphthalenedicarboxylic acids are known. In a typical process, a naphthalenedicarboxylic acid, such as 2,6-naphthalenedicarboxylic acid, is esterified with methanol at 120°-220° C. using sulfuric acid catalyst. A higher-temperature process is disclosed in U.S. Pat. No. 4,003,948 to Yamashita et al., wherein 2,6-naphthalenedicarboxylic acid is continuously esterified with methanol, in the presence or absence of an esterification catalyst, wherein the 2,6-naphthalenedicarboxylic acid is fed into an esterification reaction zone in the form of solid particles having a specific surface area of about 4,000 $cm^2/g$. For continuous operation, it is disclosed therein that a plate tower-type or a stirred vessel-type esterification reaction can be used.

Japanese Patent Application No. 50-83362 (1975) discloses a method for continuously esterifying 2,6-naphthalenedicarboxylic acid by reacting 2,6-naphthalenedicarboxylic acid with methanol while the methanol concentration in the liquid phase of the esterification reaction container is 2–20 wt. %. In the Japanese Patent Application No. 50-83362 (1975), it is disclosed that it is desirable to feed a suspension of 2,6-naphthalenedicarboxylic acid in dimethyl-2,6-naphthalenedicarboxylate to the uppermost step of a step-type column reaction container, and that methanol be fed at a position lower than the lowermost step of the step-type column. The example provided in the Japanese Patent publication describes such a counter-current addition of the reactants to the step-type reactor, and where the 2,6-naphthalenedicarboxylic acid is slurried with four times its weight of dimethyl-2,6-naphthalenedicarboxylate before it is added to the reactor. Such a process, therefore, requires a large recycle of the product to the esterification reactor. Processes for esterifying 2,6-naphthalenedicarboxylic acid are also disclosed in Japanese Patent Applications Nos. 48-96574 (1978), 50-76055 (1975), 50-76057 (1975), and 50-95253 (1975). Finally, prior processes for preparing dimethyl-terephthalate from terephthalic acid have used a two-compartment stirred tank reactor in combination with a plug-flow reactor, under essentially liquid-fill conditions and long residence times of about 1 hr, and at reaction temperatures of about 260° C.

SUMMARY OF THE INVENTION

This invention is a continuous process for preparing a dialkylester of a naphthalenedicarboxylic acid comprising passing a liquid phase reaction mixture comprising a low molecular weight alcohol, a naphthalenedicarboxylic acid and a dialkylester of a naphthalenedicarboxylic acid at an elevated temperature through series arranged reaction zones while introducing a naphthalenedicarboxylic acid and a low molecular weight alcohol to an upstream reaction zone, agitating at least one reaction zone, and removing a product comprising a dialkylester of the naphthalenedicarboxylic acid produced by the reaction of the naphthalenedicarboxylic acid with the low molecular weight alcohol from a downstream reaction zone.

It is well-recognized that the esterification of a naphthalenecarboxylic acid, such as 2,6-naphthalenedicarboxylic acid, is much more difficult than the esterification of an aromatic diacid such as terephthalic acid. For example, 2,6-naphthalenedicarboxylic acid has a very low solubility in an alcohol such as methanol and, when it is prepared by the metal catalyzed oxidation of an alkyl or acyl substituted naphthalene compound, oxidation catalyst metals are carried over with the acid into the esterification reaction. The insoluble portion of the metal catalysts, as well as the low solubility of 2,6-naphthalenedicarboxylic acid, can result in solids depositing in the esterification reactor and plugging the reactor. The process of the present invention, however, minimizes the adverse effects of these insoluble components.

Additionally, under reaction conditions used for preparing dialkylesters of naphthalenedicarboxylic acids, particularly prior art processes wherein a strong acid catalyst such as sulfuric acid is used, an undesirable side reaction occurs where the alcohol, such as methanol, is convened to a diaikylether, such as dimethylether. Such dimethylether formation consumes methanol that could otherwise be recycled and the dimethylether also presents a disposal problem. Furthermore, the water formed concomitantly with the dimethylether limits the equilibriumcontrolled esterification reaction. Using the present process, however, a naphthalenedicarboxylic acid such as 2,6-naphthalenedicarboxylic acid can be esterified with methanol without forming excessive amounts of dimethylether.

BRIEF DESCRIPTION OF THE DRAWING

The figure shows a cross-sectional view of a preferred reactor for practicing the process of the invention.

DETAILED DESCRIPTION OF THE INVENTION

Figure 1:
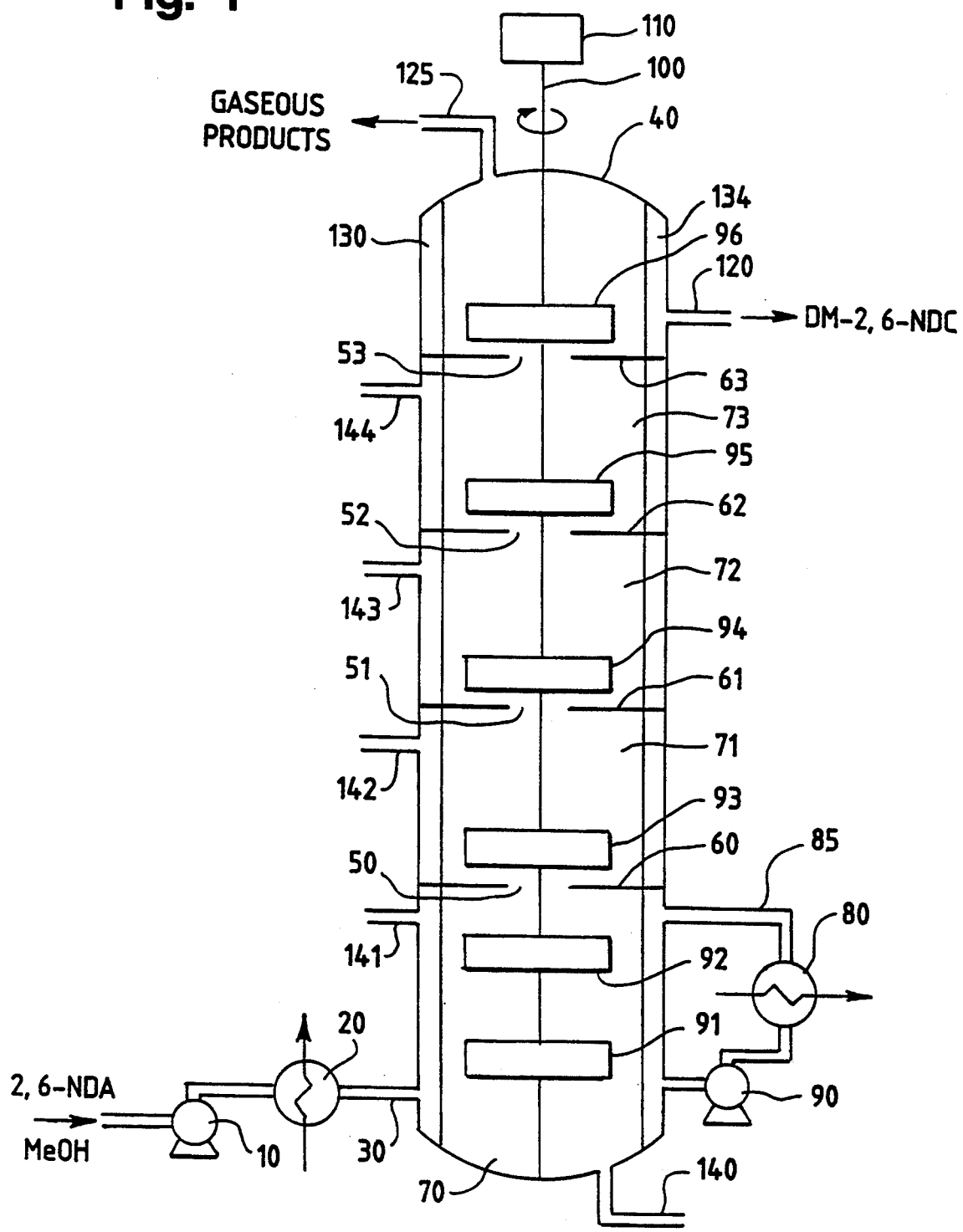

In the process of this invention, a naphthalenedicarboxylic acid is esterified with a low molecular weight alcohol at an elevated temperature using at least two and, preferably greater than two, series arranged reaction zones, wherein the series arranged reaction zones are provided with a means for allowing at least a portion of the reaction mixture to flow from one reaction zone to the next in the series. We have determined that such an arrangement of reactors provides for the rapid esterification of a naphthalenedicarboxylic acid, such as 2,6-naphthalenedicarboxylic acid, with a low molecular weight alcohol such as methanol.

Also, in the process of this invention the alcohol and the naphthalenedicarboxylic acid are added in a co-current manner, i.e., the alcohol and naphthalenedicarboxylic acid are added to one or more upstream reaction zones and the product ester is removed from a downstream reaction zone. Using this arrangement, the high melting, generally insoluble naphthalenedicarboxylic acid can be slurried with the alcohol, thereby eliminating the need for a large excess of dialkylester of the naphthalenedicarboxylic acid as a slurry medium as would be required for the prior art, counter-current addition of the alcohol and naphthalenedicarboxylic acid feed materials to the esterification reaction mixture.

In a preferred mode of operating the process of this invention, reaction conditions are selected such that most of the alcohol, typically methanol, added to the reaction mixture is in the gaseous or vapor phase in the series arranged reaction zones thereby allowing the alcohol to move rapidly through the reaction zones. Operation at these reaction conditions allows for the use of a smaller esterification reactor volume compared to a process where all of the alcohol added is in the liquid phase in the reaction mixture. Importantly, the presence of the gaseous alcohol moving through the series arranged reaction zones provides for the efficient removal of water from the esterification reaction thereby shifting the equilibrium so that the desired dialkylester is formed more readily. When most of the alcohol added to the reaction mixture is present in the series arranged reaction zones is in the gas phase, the formation of a dialkylether, such as dimethylether, can be reduced.

In the process of this invention, at least one of the reaction zones is equipped to provide agitation of the esterification reaction mixture contained therein. While the agitation can be in at least one reaction zone, it is preferable that each reaction zone has agitation to promote the suspension of the solid components of the esterification reaction mixture, thereby increasing the contact between the liquid and solid phases present and, most importantly, preventing deposition of the solids that are present during the esterification reaction. When a gas phase of the alcohol is present in the esterification reactor, the agitation improves contact between the liquid and gas phases. Improved contact between the liquid and gas phases allows for the dissolution of gaseous alcohol into the liquid phase as well as transfer of water from the liquid phase into gas phase. This addition of alcohol and removal of water promotes the esterification reaction.

The naphthalenedicarboxylic acids useful in the method of this invention are selected from: 1,2-, 1,3-, 1,4-, 1,5-, 1,6-, 1,7-, 1,8-, 2,3-, 2,6-, or 2,7-naphthalenedicarboxylic acid, however, 2,6- and 2,7-naphthalenedicarboxylic acid are preferred. Most preferred is 2,6-naphthalenedicarboxylic acid. Any known method for preparing these naphthalenedicarboxylic acids can be used. The process of this invention is particularly suitable for esterifying a naphthalenedicarboxylic acid prepared by the liquid phase, heavy metal catalyzed oxidation of a dialkyl- or alkyl-acylnaphthalene compound. Such dialkyl or alkylacylnaphthalene compounds that can be oxidized by a liquid phase, heavy metal catalyzed oxidation reaction include components having structure:

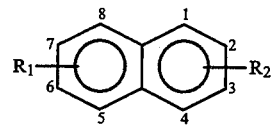

wherein $R_1$ and $R_2$ are independently selected from a hydrocarbyl group having 1 to about 6 carbon atoms, an acyl group having 2 to about 6 carbon atoms or a formyl group. Specific examples of such naphthalene compounds include 2,6-dimethylnaphthalene, 2-methyl-6-acetylnaphthalene, 2-methyl-6-butrylnaphthalene, 1,4-dimethylnaphthalene, 2,3-dimethylnaphthalene, 2,6-diethylnaphthalene, 2,6-diisopropylnaphthalene and the like. Sikkenga et al. U.S. Pat. Nos. 5,034,561; 5,030,781 and 4,950,825 disclose methods for preparing dimethylnaphthalene, in Hagen et al. U.S. Pat. No. 5,026,917, a process for preparing 2-methyl-6-acetylnaphthalene is disclosed, and in Hagen et al., U.S. Pat. No. 4,873,386, a process for preparing 2,6-diethylnaphthalene is disclosed.

The most preferred aromatic feed compound for preparing the naphthalenedicarboxylic acid is 2,6-dimethylnaphthalene. Oxidation of 2,6-dimethylnaphthalene produces 2,6-naphthalenedicarboxylic acid which, as described hereinabove, is a suitable monomer for preparing PEN, a high-performance polyester. Furthermore, 2,6-dimethylnaphthalene is superior to, for example, 2,6-diethyl- or 2,6-diisopropylnaphthalene because it is lower in molecular weight and the yield of 2,6-naphthalenedicarboxylic acid per given weight of 2,6-dialkylnaphthalene compound is greater for 2,6-dimethylnaphthalene than for 2,6-diethyl- or 2,6-diisopropylnaphthalene.

Methods for conducting the liquid phase, heavy metal catalyzed oxidation of an alkyl- or acyl-substituted aromatic compound - such as the naphthalene compounds described hereinabove - to the corresponding aromatic carboxylic acid are well known in the art. For example, U.S. Pat. Nos. 4,950,786; 4,933,491; 3,870,754 and 2,833,816 disclose such oxidation methods. In general, suitable heavy metal oxidation catalysts include those metals having an atomic number of about 21 to about 82, inclusive. The preferred oxidation solvent is a low molecular weight monocarboxylic acid having 2 to about 8 carbon atoms, inclusive, preferably it is acetic acid or mixtures of acetic acid and water. A promoter such as a low molecular weight ketone having 2 to about 6 carbon atoms or a low molecular weight aidehyde having 1 to about 6 carbon atoms can also be used. Bromine promoter compounds known in the art such as hydrogen bromide, molecular bromine, sodium bromide and the like can also be used. A source of molecular oxygen is also required, and typically it is air.

A particularly suitable method for oxidizing dialkyl or alkylacylnapthalene compounds, and particularly 2,6-dimethylnaphthalene, to naphthalenedicarboxylic acids is disclosed in U.S. Pat. No. 4,933,491 to Albertins et al. Suitable solvents for such liquid phase oxidation reaction of dialkyl or alkylacylnapthalene compounds include low molecular weight carboxylic acids such as benzoic acid, any aliphatic $C_2$–$C_6$ monocarboxylic acid such as acetic acid, propionic acid, n-butyric acid, isobutyric acid, n-valeric acid, trimethylacetic acid, caproic acid, and water. Preferably the solvent is a mixture of water and acetic acid, which mixture is preferably 1 to 20 weight percent water. The source of molecular oxygen employed in such liquid phase oxidation of the dialkyl or alkylacylnapthalene compounds can vary in molecular oxygen content from that of air to oxygen gas. Because of economy, air is the preferred source of molecular oxygen.

The catalyst employed in such oxidation of the dialkyl or alkylacylnapthalene compounds comprises a bromine-containing compound and at least one of a cobalt- and manganese-containing compound. Preferably, the catalyst comprises cobalt-, manganese-, and bromine-containing components. The ratio of cobalt (calculated as elemental cobalt) in the cobalt component of the catalyst to dialkyl or alkylacylnapthalene compound in the liquid phase oxidation is in the range of about 0.1 to about 100 milligram atoms (mga) per gram mole of dialkyl or alkylacylnaphthalene compound. The ratio of manganese (calculated as elemental manganese) in the manganese component of the catalyst to cobalt (calculated as elemental cobalt) in the cobalt component of the catalyst in the liquid phase oxidation is in the range of from about 0.1 to about 10 mga per mga of cobalt. The ratio of bromine (calculated as elemental bromine) in the bromine component of the catalyst to total cobalt and manganese (calculated as elemental cobalt and elemental manganese) in the cobalt and manganese components of the catalyst in the liquid phase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 1.5:1.0 bromine to total cobalt and manganese milligram atom ratio is provided by a suitable bromine source such as elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzylbromide, tetrabromoethane, ethylenedibromide, etc.). The total bromine in molecular bromine and ionic bromide is used to determine satisfaction of the elemental bromine to total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 335° F. to 440° F., has been found to yield about 3 effective gram atoms of bromine per gram mole.

In operation, the minimum pressure at which the oxidation reactor is maintained is that pressure which will maintain a substantial liquid phase of the dialkyl or alkylacylnapthalene compound and at least 70 weight percent of the solvent. The dialkyl or alkylacylnapthalene compound and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 atmosphere to about 35 atmospheres, and typically are in the range of from about 10 atmospheres to about 30 atmospheres. The temperature range within the oxidation reactor is generally from about 250° F., preferably from about 350° F. to about 450° F., preferably to about 420° F. The solvent residence time in the oxidation reactor is generally from about 20 to about 150 minutes and preferably from about 30 to about 120 minutes.

The oxidation can be performed either in a batch, continuous, or semicontinuous mode. In the batch mode, the dialkyl or alkylacylnapthalene compound, solvent and the catalyst components are initially introduced batchwise into the reactor, and the temperature and pressure of the reactor contents are then raised to the desired levels for the commencement of the oxidation reaction. Air is introduced continuously into the reactor. After commencement of the oxidation reaction, for example, after all of the dialkyl or alkylacylnapthalene compound has been completely introduced into the reactor, the temperature of the reactor contents is raised. In the continuous mode, each of the dialkyl or alkylacylnapthalene compound, air, solvent, and catalyst are continuously introduced into the reactor, and a product stream comprising naphthalenedicarboxylic acid and catalyst components dissolved in the solvent is withdrawn from the reactor. In the semicontinuous mode, the solvent and catalyst are initially introduced into the reactor and then the dialkyl or alkylacylnapthalene compound and air are continuously introduced into the reactor. For large-scale commercial operation it is preferable to use a continuous oxidation process. In such a process using 2,6-dimethylnaphthalene as the feed, the weight ratio of monocarboxylic acid solvent to 2,6-dimethylnaphthalene is preferably about 2:1 to about 12:1, the mga ratio of manganese to cobalt is about 5:1 to about 0.3:1, the mga ratio of bromine to the total of cobalt and manganese is about 0.3:1 to about 0.8:1, and the total of cobalt and manganese, calculated as elemental cobalt and elemental manganese is at least about 0.40 weight percent based on the weight of the solvent, and the oxidation reaction temperature is about 370° F. to about 420° F. Acetic acid is the most suitable solvent for such preferred continuous oxidation of 2,6-dimethylnaphthalene.

Subsequent to the oxidation reaction, the oxidation reaction mixture is typically cooled to promote the crystallization of the naphthalenedicarboxylic acid from the reaction mixture; and the naphthalenedicarboxylic acid is partitioned (i.e. separated) from the oxidation reaction mixture by any suitable means for separating a solid from a liquid phase, for example, by centrifugation, filtration and the like. The separated naphthalenedicarboxylic acid can be washed with one or more solvents either at ambient or, preferably, an elevated temperature. Most suitably the wash solvent is water, acetic acid or other low molecular weight aliphatic carboxylic acid or mixtures of water and a low molecular weight carboxylic acid. The crude naphthalenedicarboxylic acid can be dried before esterification.

The alcohols that are useful in the esterification process of this invention are low-molecular weight alcohols having 1 to about 6 carbon atoms, for example: methanol, ethanol, n-propanol, isopropanol, n-butanol, isobutanol, n-pentanol, n-hexanol, and the like. Most preferably, due to cost and the lower molecular weight of the resulting ester, the alcohol used for the esterification of the naphthalenedicarboxylic acid is methanol. The amount of methanol or other low-molecular weight alcohol that is reacted with the naphthalenedicarboxylic acid is an amount sufficient to convert a major portion of the naphthalenedicarboxylic acid to the diester. For example, the weight ratio of alcohol to naphthalenedicarboxylic acid added to the reactor is suitably about 1:1 to about 10:1; more preferably, 2:1 to about 6:1. A large molar excess of alcohol relative to the free carboxylic acid groups can provide for a more complete conversion of the naphthalenecarboxylic acid to diester; however, the larger amount of alcohol requires the use of a large reaction mixture volume, which requires a larger reactor or slower throughput. Additionally, the excess methanol must be separated and recycled. It is, therefore, more advantageous to use lower weight ratios of alcohol to naphthalenedicarboxylic acid, such as about 1:1 to about 10:1, more preferably, 2:1 to about 6:1.

The alcohol and naphthalenedicarboxylic acid are added to the esterification reactor to a reaction zone or reaction zones upstream from the reaction zone where the product mixture comprising the diester of the naphthalenedicarboxylic acid is removed from the series arranged reaction zones. The alcohol and the naphthalenedicarboxylic acid are preferably added as a mixture. However, the naphthalenedicarboxylic acid and the low-molecular weight alcohol can be added separately.

Alternatively, only part of the alcohol can be added with the naphthalenedicarboxylic acid and the remainder of the alcohol added separately. Thus, in the process of this invention, any suitable method for adding the alcohol and naphthalenedicarboxylic acid feed components to the esterification mixture is contemplated. However, it is most preferable to add the naphthalenedicarboxylic acid to the reaction mixture as a slurry with the alcohol, which slurry can be pumped into or otherwise added to the reaction mixture. By using the alcohol to slurry the solid naphthalenedicarboxylic acid, it is possible to add the naphthalenedicarboxylic acid to the reaction mixture without using recycled diester to slurry the naphthalenedicarboxylic acid. This is one of the advantages of the present invention. In the prior art processes where the alcohol and the naphthalenedicarboxylic acid are added counter-currently, rather than co-currently, the naphthalenedicarboxylic acid had to be slurried with a relatively large amount of diester. Consequently, a large part of the crude diester product would need to be recycled to the front end of the process to provide the slurry medium for the fresh naphthalenedicarboxylic acid. Such recycle is an inefficient operation. In contrast, in the instant invention with the cocurrent addition of the alcohol and the naphthalenedicarboxylic acid, there is enough conversion to the diester of the naphthalenedicrboxylic acid in the initial upstream reaction zone to provide a liquid medium for the esterification reaction. The weight ratio of alcohol to naphthalenedicarboxylic acid in the slurry is suitably about 1:1 to about 10:1, preferably about 1.5:1 to about 6:1.

In the preferred process, the mixture of alcohol and naphthalenedicarboxylic acid is first pre-heated before the mixture is added to the series arranged esterification reaction zones. A stirred tank reactor, a tubular heat exchanger, or a combination thereof can function as a preheater. The preheater heats the mixture of alcohol and naphthalenedicarboxylic acid to a temperature typically below the esterification temperature. For example, temperatures in the range of about 300° F. to about 700° F. are suitable. When methanol is used, the temperature of the preheater is preferably below the critical temperature of methanol. All of the alcohol charged to the esterification reaction mixture can be added through the preheater. Alternatively, only pan of the total alcohol charged to the mixture is added through the preheater, and the remainder is added to the esterification reaction mixture either directly or through a separate preheater.

The naphthalenedicarboxylic acid can also be added to the esterification reaction mixture or, if used, the preheater, along with a monoalkyl ester of a naphthalenedicarboxylic acid, a dialkylester of a naphthalenedicarboxylic acid, or a combination of mono- and dialkylester of naphthalenedicarboxylic acid. If used, the weight ratio of the mono- or dialkyl naphthalenedicarboxylic acid ester (or mixture thereof) to naphthalenedicarboxylic acid is suitably about 0.01:1 to about 1:1; more preferably, about 0.1:1 to about 0.5:1. The naphthalenedicarboxytic acid can be premixed with the mono- and/or dialkylester of naphthalenedicarboxylic acid before it is added to the reactor or preheater. Alternatively, the naphthalenedicarboxylic acid can be added to the reactor or preheater separately from the addition of the mono- and/or dialkyl ester of naphthalenedicarboxylic acid.

We have determined that esterification reaction temperatures in the range of about 500° F. to about 700° F., preferably about 540° F. to about 660° F., provide for rapid reaction rates without significant decomposition of the starting naphthalenedicarboxylic acid or dialkylester product. At these high reaction temperatures, the esterification reaction is rapid and long reaction residence times are not required. Each reaction zone may be operated at the same, or at different temperatures.

The pressure used for the esterification reaction is suitably in the range of about 5 to about 250; preferably, about 20 to about 150 atmospheres absolute. When practicing the process of this invention, it is preferable to use reaction conditions such as temperature and pressure, so that the reactor is not completely liquid-filled, i.e., where there is at least some alcohol present is in the gaseous phase in the reactor rather than having all of the alcohol be present in the liquid phase. When practicing this preferred mode, one reaction zone, rather a series of zones, can be used. It is preferable, however, to use at least two reaction zones in series. Thus, in the preferred series arranged zones, one or more reaction zone preferably contains a gaseous alcohol stream moving through the reaction zone, preferably through the liquid component of the reaction mixture, the liquid component being mainly the product dialkylester of naphthalenedicarboxylic acid along with varying amounts of the mono ester of the naphthalenedicarboxylic acid. When operating within conditions where a portion of the alcohol is in the gaseous phase, we have determined that a much smaller total reactor volume can be used to complete the esterification reaction. Under conditions where part of the alcohol is in the gas phase, the gaseous alcohol can move through the series arranged reaction zones very rapidly, and the reactor volume can be used more efficiently. The result being a much smaller reactor volume can be used. Additionally, the gaseous alcohol, preferably methanol, moving through the single reaction zone or preferably the series arranged reaction zones, removes a portion of the water formed during the esterification reaction and allows for a greater conversion of the diacid to the desired dialkylester. Furthermore, we have determined that when the esterification reaction is conducted such that a major portion of the alcohol added to the reaction mixture is in the gaseous state, there is only a very low formation of dialkylether. Apparently, most of the dialkylether formation occurs in a liquid phase reaction, possibly catalyzed by the acidic esterification reaction mixture. By suitably adjusting reaction conditions, such as reaction temperature and reaction pressure, it is highly advantageous to operate such that about 50 to about 99%, preferably about 80 to about 98%, of the alcohol charged to the reaction mixture is in the vapor or gaseous state rather than being liquid in the esterification reactor. Thus, by suitably adjusting reaction conditions and after correcting for alcohol consumed in the esterification reaction, the ratio of the rate of gaseous alcohol, preferably methanol, passing through the esterification reaction zones from the upstream to the downstream reaction zone, and preferably through the liquid phase of the esterification reaction mixture, in pounds per hour, to the rate of addition of alcohol to the reaction mixture in pounds per hour, is about 0.5:1 to about 0.99:1, preferably about 0.8:1 to about 0.98:1. Stated differently, preferably about 50 to about 99%, more preferably about 80 to about 98% of the total alcohol exiting a reactor zone in the esterification reactor, is in the gaseous state. Suitable pressures for such operation are in the range of about 5 atmospheres absolute to about 250 atmospheres absolute, along with temperatures in the range of about 500° F. to about 700° F.

The esterification reaction according to the process of this invention can be conducted with or without one or more standard esterification catalysts. However, it is preferable not to use an esterification catalyst. One of the advantages of the process of this invention is the ability to conduct the esterification reaction without the addition of an esterification catalyst. Thus, the preferred mode of operating the process of this invention is to conduct the esterification reaction in the substantial and, more preferably, complete absence of an esterification catalyst. Should one or more standard esterification catalysts be included, it is preferable to use molybdenum trioxide, zinc, zinc oxide, a titanate ester, or an organo tin compound. A suitable selection of metal-based esterification catalysts is disclosed in British Patent Specification 1,437,897.

The residence time for the liquid portion of the esterification reaction mixture in the process of this invention is suitably about 0.1 hours to about 10 hours, more preferably about 0.1 hours to about 2 hours.

In the process of this invention, two reaction zones in series can be used to perform the esterification reaction. Preferably, about 2 to about 20, most preferably about 3 to about 15, reaction zones are used in series. The reaction zones are equipped such that the esterification reaction mixture can flow between zones from the initial reaction zone to the terminal reaction zone. At least one of the reaction zones is agitated to provide for the suspension of the solids present in the reaction zone. Preferably, all of the reaction zones are agitated with a suitable stirrer or other means for agitating a liquid phase. A pump circulating the liquid phase within the reaction zone can also serve to agitate the contents of a reaction zone. The reaction zones are suitably tank reactors, preferably stirred tank reactors, plug flow reactors, or a combination of these or other reactors. As discussed in more detail below, a particularly preferred configuration for the series arranged reaction zones is a vertically arranged compartmented reactor having two or more compartments segregated by a divider plate or other separating means that allows for the passage of the esterification reaction mixture from a lower compartment to an upper compartment. As described below, one such compartmented reactor having a plurality of compartments can be used. Alternatively, two or more of such compartmented reactors can be used in series to achieve series arranged reaction zones according to the process of this invention. Regardless of the specific apparatus used for a reaction zone, the reactors must be able to withstand the temperatures and pressures used in the process of this invention. Also, the construction of the reactors should be such that it will withstand the effects of exposure to the corrosive esterification reaction mixture. Consequently, the parts of the reactor vessels exposed to the esterification reaction mixture can be manufactured of materials such as 316 stainless steel or a nickel-based alloy, such as Hastelloy C. The reaction zones can have equal or different volumes. Preferably, the first reaction zone is larger than the subsequent zones so that it provides for a longer residence time and greater conversion of the naphthalenedicarboxylic acid to diester.

The preferred reactor configuration is a vertically arranged, cylindrical vessel that is divided into at least an upper and a lower compartment, each compartment functioning as a reaction zone. Preferably, the vessel is divided into about 2 to about 20, most preferably about 3 to about 15 compartments. Each compartment is separated from the adjacent compartment by a plate or other suitable means for dividing the reactor vessel into compartments. Each plate or other divider means is provided with at least one opening to allow for the passage of liquid, solid and, if present, gaseous components of the esterification reaction mixture from one compartment to the next, while the esterification reaction mixture passes in an upward direction through the reactor vessel. The low molecular weight alcohol and the naphthalenedicarboxylic acid are added to a lower compartment and a reaction product mixture containing the diester of the naphthalenedicarboxylic acid is removed from an upper reactor compartment. The area of the opening relative to the area of the divider plate is such that the esterification reaction mixture can pass through the opening without causing a excessive back-pressure, and yet prevent substantial back-flow of the esterification reaction mixture to the previous compartment. A suitable opening in the divider plate comprises about 0.1 to about 10% of the area of the dividing plate or other dividing means. In a preferred embodiment, an agitator shaft runs vertically through the reactor vessel, preferably along the center line of the reactor vessel (if it is a cylindrical vessel) and at least one agitator is attached to the agitator shaft in at least one and, preferably, all of the compartments. An agitator located in each compartment provides for mixing and the suspension of insoluble matter in the esterification reaction mixture that would otherwise lead to the formation of deposits that could decrease the reactor volume, severely restrict the flow of the esterification reaction mixture and eventually plug the reactor. The reactor vessel can also be equipped with baffles positioned within one or more of the compartments. One configuration is to have the baffles positioned so that they are normal to the inside surface of the reactor and run the entire length of the reactor. Other configurations of the baffles are also suitable, for example, the baffles can extend only part way from the bottom of each compartment.

DETAILED DESCRIPTION OF THE DRAWING

The Figure depicts, in a cross-sectional view, a preferred esterification reactor apparatus for operating the process of this invention. In the following description, the naphthalenedicarboxylic acid esterified is 2,6-naphthalenedicarboxylic acid and the alcohol is methanol. Referring to the Figure, a 4:1:0.2 by weight mixture, in the form of a slurry, of 2,6-naphthalenedicarboxylic acid (2,6-NDA), methanol (MeOH) and dimethyl-2,6-naphthalenedicarboxylate (DM-2,6-NDC), respectively, are added to pump 10 which pumps the slurry into heat exchanger 20, which increases the temperature of the slurry to a temperature below that of esterification reaction mixture and, typically, below the critical temperature of methanol. Heat exchanger 20 can be a tubular heat exchanger, or stirred tank reactor. The slurry exiting heat exchanger 20 enters compartmented esterification reactor 40 through line 30. The reaction mixture in reactor 40 flows upward through the compartments through openings 50-53 in divider plates 60-63. Reaction mixture present in lower compartment 70 is heated to the reaction temperature using heat exchanger 80. The esterification reaction mixture is circulated from lower compartment 70 through heat exchanger 80 using pump 90 and line 85. The esterification reaction mixture within the reactor is stirred by agitators 91-96, connected to agitator shaft 100. Agitator shaft 100 is rotated by variable speed motor 110. Product mixture comprising DM-2,6-NDC is removed from reactor vessel 40 through product mixture port 120, and gaseous reaction products such as methanol, water, and dimethylether, if formed, are removed through vapor exit port 125. The opening 120 in reactor 40 for product mixture is below the liquid level in the reactor. Reactor 40 is also equipped with baffle plates 130 and 134 (baffle plates 131 and 133 are not shown in the Figure). Auxiliary ports 140-144 can be used to add additional methanol, 2,6-naphthalenedicarboxylic acid, and/or dimethyl-2,6-naphthalenedicarboxylate. Agitator blades 91 and 93-96 are preferably located close to the bottom of the compartment in order to maintain the solids present in the reaction in suspension. The agitator blades can be any suitable shape or configuration, such as straight or pitch-blade turbines, or marine propellers, or a combination thereof. Paddle-type agitator blades are shown in the Figure. Baffle plates 130-134, if used, can be attached to the inside surface of the reactor along the full length of the baffle plate. Alternatively, the baffle plates can be spaced slightly from the reactor wall in order to prevent the accumulation of deposits. Variable speed motor 110 permits operation at a continuous range of rotational speeds. The product mixture exiting reactor 40 comprises primarily dimethyl-2,6-naphthalenedicarboxylate and mono-methyl-2,6-naphthalenedicarboxylic acid.

in a typical mode of practicing the process of this invention using the preferred reactor shown in the Figure, a 4:1 mixture (by weight) of methanol to 2,6-NDA is added to reactor compartment 70 through heat exchanger 20. The slurry of 2,6-NDA in methanol is heated in the heat exchanger to a temperature of about 450° F. The reactor contents are maintained at a temperature of about 600° F. and a pressure of about 85 atmospheres absolute. In compartment 70, most of the methanol pumped in with the slurry in the feed is vaporized. Enough 2,6-NDA (e.g., >50%)is, however, converted to the mono-methylester of 2,6-NDA and the diester in the first compartment to keep the slurry pumpable. Most of the by-product water goes into the vapor phase. The resulting mixture of vapor, liquid, and solid (2,6-NDA and insolubles) passes through aperture 50 into next compartment 71, where additional methanol dissolves in the liquid phase and additional by-product water is stripped out of the liquid phase to allow fuller conversion of the 2,6-NDA to the mono- and dimethylester. This process is continued in the following compartments 72 and 73, until most of the 2,6-NDA and monomethylester have been converted to dimethyl-2,6-naphthalenedicarboxylate in the terminal compartment 74. The entire product can be withdrawn through a port near the top of the last compartment (not shown), or the liquid containing most of the dimethyl-2,6-naphthalenedicarboxylate can be removed through port 120, and the vapor containing most of the methanol and water can be removed through port 125.

The amount of the mono-methyl ester present in the product mixture depends on a number of variables, such as the molar ratio of methanol to naphthalenedicarboxylic acid, the reaction temperature, and the residence time of the reaction mixture in the reactor. Generally, the process of this invention produces an ester such as dimethyl-2,6-naphthalenedicarboxylate having about 1 to about 10 wt. % mono-methyl-2,6-naphthalenedicarboxylate, more preferably, about 0.01 to about 6 wt. % mono-methyl-2,6-naphthalenedicarboxylate.

The diester of naphthalenedicarboxylic acid produced by the process of this invention will ordinarily require purification by one or more purification procedures such as recrystallization, distillation, and combinations thereof. In the purification process, the reactor effluent is typically cooled to crystallize any dissolved diester, and the diester is separated from the residual alcohol and washed with alcohol to remove adhering mother liquor. The diester can be purified by recrystallization, distillation, or any combination thereof. Filtrates and distillation bottoms from the purification process may contain oxidation catalyst metals carried over from oxidation reaction used to prepare the naphthalenedicarboxylic acid. Those filtrates and distillation bottoms can be concentrated and washed with hot low molecular weight carboxylic acid, such as acetic acid, to recover an acid solution of the catalyzed metals. The acid solution can be concentrated or used as is for the oxidation reaction.

The following examples are being presented to facilitate an understanding of the process of the present invention, without intending to limit the scope thereof.

EXAMPLES

In the following examples, TMLA is trimellitic acid, 2,6-NDA is 2,6-naphthalenedicarboxylic acid, Br-2,6-NDA is brominated 2,6-naphthalenedicarboxylic acid, FNA is 2-formyl-6-naphthoic acid, TMTM is trimethyl-trimellitate, 2-NA is 2-naphthoic acid, MM-2,6-NDC is the mono methylester of 2,6-naphthalenedicarboxylic acid, MeFNA is the methylester of 2-formyl-6-naphthoic acid, Me2-NA is the methylester of 2-naphthoic acid, DM-2,6-NDC is the dimethylester of 2,6-naphthalenedicarboxylic acid, Br-2,6-NDC is a brominated dimethylester of 2,6-naphthalenedicarboxylic acid, and DME is dimethylether. Also, NA means not analyzed, and ND means not detected. Since the liquid chromatography method used to analyze the products in the following examples was tuned to high accuracy for the minor components, there is some error in the values reported for the major components. Consequently, the totals in the tables do not add up to 100%.

EXAMPLE 1

A series of experiments were conducted using 2,6-naphthalenedicarboxylic acid and methanol to demonstrate that rapid esterification rates are obtained at elevated reaction temperature without the formation of excessive amounts of reaction decomposition products such as 2-methylnaphthoate or 2-naphthoic acid, and without the formation of excessive amounts of dimethylether.

A 50 ml pressure vessel fitted with an internal thermocouple was charged with 7.8 g MeOH, 0.2 g water and only 2 g of a mixture of solids containing 40–43% of 2,6-NDA and 44–45% DM-2,6-NDC. The vessel was purged with helium, sealed, then with vigorous shaking was immersed into a heated sand bath to attain the desired reaction temperature within 2 min. After maintaining the reactor at the desired conditions, the reactor was removed from the sand bath and cooled rapidly in a stream of compressed air. The methanol phase was analyzed for the dimethylether content and the solid product was analyzed by liquid chromatography to determine the extent of acid group conversion. The mole percent of acid group conversion (including 2,6-NDA and the monomethyl ester) is listed at the bottom of Table 1. The feedstock contained about 3% unreactive 2,6-NDA due to formation of the 2,6-NDA metal salts from the oxidation catalyst that remained in the 2,6-NDA. This unreacted 2,6-NDA appears in all product analyses.

Runs 1–4 were conducted at a temperature of 530° F. The results in Table 1 indicate that a residence time of 5 min yielded 27% acid conversion, 10 min yielded 60% conversion, and 20 min yielded 87% conversion. The weight percent of DME ranged from 0.12 to 0.5% for these runs.

Runs 5–9 were conduced at 600° F., as shown in Table 1. As was found for the runs at 530° F., the extent of acid group conversion varied with the reaction time. However, the higher temperature resulted in much higher esterification rates so that 90% acid group conversion was obtained in only 10 min, compared to 20 min at 530° F. Most importantly, however, was the fact that the higher temperature did not accelerate the rate of DME formation as much as the rate of esterification.

TABLE 1

| RUN #[a] | | 1 | 2 | 3 | 4 | | 5 | 6 | 7 | 8 | 9 |
|---|---|---|---|---|---|---|---|---|---|---|---|
| REACTION CONDITIONS[d] | 2,6-NDA[b] Feedstock | | | | | 2,6-NDA[c] Feedstock | | | | | |
| Temperature (°F.) | | 530 | 530 | 530 | 530 | | 600 | 600 | 600 | 600 | 600 |
| Residence Time (minutes) | | 0 | 5 | 10 | 20 | | 0 | 1 | 2 | 5 | 10 |
| PRODUCT (OR 2,6-NDC) ANALYSIS | | | | | | | | | | | |
| Weight of Product (g) | | 10.02 | 9.65 | 10.15 | 10.18 | | 9.73 | 10.08 | 9.68 | 9.69 | 10.03 |
| Weight Percent Loss (gain) | | 0.00 | 3.50 | (1.50) | (1.80) | | 2.70 | (0.80) | 3.30 | 3.10 | (0.31) |
| Dry Weight (g) | | 1.92 | 1.92 | 1.99 | 2.03 | | 1.87 | 2.01 | 2.00 | 1.99 | 2.02 |
| ANALYSIS OF DRY PRODUCT (WT. %) | | | | | | | | | | | |
| TMLA | 1.04 | 0.06 | 0.01 | 0.00 | 0.00 | 0.71 | 0.06 | 0.00 | 0.00 | 0.00 | 0.00 |
| 2,6-NDA | 40.23 | 40.60 | 22.07 | 7.21 | 3.10 | 42.46 | 34.24 | 11.64 | 6.80 | 3.45 | 2.97 |
| Br-2,6-NDA | 0.29 | 0.21 | 0.08 | 0.02 | 0.00 | 0.28 | 0.15 | 0.04 | 0.00 | 0.00 | 0.00 |
| FNA | 0.15 | 0.12 | 0.06 | 0.02 | 0.00 | 0.15 | 0.09 | 0.05 | 0.03 | 0.00 | 0.00 |
| TMTM | 1.39 | 0.37 | 1.18 | 0.53 | 0.86 | 0.78 | 0.76 | 0.96 | 1.03 | 1.39 | 1.03 |
| 2-NA | 0.09 | 0.05 | 0.05 | 0.03 | 0.04 | 0.00 | 0.00 | 0.00 | 0.00 | 0.02 | 0.00 |
| MM-2,6-NDC | 8.31 | 8.74 | 15.21 | 17.63 | 3.74 | 8.00 | 11.76 | 23.45 | 18.19 | 5.19 | 2.57 |
| MeFNA | 0.17 | 0.09 | 0.14 | 0.15 | 0.14 | 0.12 | 0.12 | 0.16 | 0.17 | 0.18 | 0.14 |
| Me2NA | 0.03 | 0.00 | 0.02 | 0.01 | 0.00 | 0.02 | 0.00 | 0.00 | 0.02 | 0.00 | 0.00 |
| DM-2,6-NDC | 44.82 | 45.24 | 57.11 | 68.14 | 84.02 | 44.46 | 48.76 | 59.82 | 67.31 | 83.19 | 87.47 |
| Br-2,6-NDC | 0.31 | 0.16 | 0.23 | 0.21 | 0.03 | 0.18 | 0.18 | 0.20 | 0.26 | 0.28 | 0.16 |
| Others | 1.98 | 1.45 | 1.39 | 1.26 | 1.72 | 0.96 | 1.94 | 1.54 | 1.43 | 1.35 | 2.92 |

TABLE 1-continued

| RUN #[a] | | 1 | 2 | 3 | 4 | | 5 | 6 | 7 | 8 | 9 |
|---|---|---|---|---|---|---|---|---|---|---|---|
| TOTAL WT. % | 98.80 | 97.10 | 97.55 | 95.21 | 93.65 | | 98.07 | 98.07 | 97.86 | 95.24 | 96.07 | 97.26 |
| ANALYSIS OF DRY PRODUCT (Mole %) | | | | | | | | | | | |
| 2,6-NDA | | 45.49 | 25.07 | 8.51 | 3.78 | | 47.53 | 38.38 | 13.29 | 8.04 | 4.09 | 3.55 |
| MM 2,6-NDC | | 9.20 | 16.22 | 19.55 | 4.29 | | 8.41 | 12.38 | 25.14 | 20.22 | 6.90 | 2.88 |
| DM-2,6-NDC | | 44.86 | 57.40 | 71.22 | 90.85 | | 44.06 | 48.37 | 60.44 | 70.49 | 87.37 | 92.35 |
| Total Acid Groups | | 50.09 | 33.18 | 18.29 | 5.93 | | 51.74 | 44.57 | 25.86 | 18.15 | 7.55 | 4.99 |
| Total Ester Groups | | 49.46 | 65.51 | 80.99 | 92.99 | | 48.26 | 54.56 | 73.01 | 80.60 | 90.82 | 93.79 |
| METAL ANALYSIS OF FEEDSTOCK (WT. %) | | | | | | | | | | | |
| Cobalt | 0.12 | | | | | | 0.11 | | | | | |
| Manganese | 0.68 | | | | | | 0.69 | | | | | |
| Bromine | 0.32 | | | | | | 0.32 | | | | | |
| FILTRATE ANALYSIS | MeOH Feed | | | | | | MeOH Feed | | | | | |
| Weight Percent DME | 0.00 | 0.04 | 0.12 | 0.25 | 0.50 | | 0.00 | 0.04 | 0.12 | 0.15 | 0.20 | 0.39 |
| Weight Percent H2O | 2.15 | 2.63 | 2.72 | 3.89 | 4.50 | | 2.15 | 2.45 | 3.72 | 3.59 | 3.17 | 4.40 |
| MOLE % ACID GROUP CONVERSION | | 0.00 | 27.0 | 59.8 | 87.0 | | | 13.9 | 50.0 | 64.9 | 85.4 | 90.4 |

[a]All reactions are conducted using 7.83 g of methanol, 2.0 g of the 2,6-NDA/DM-2,6-NDC mixture and 0.17 g of water. The 2,6-NDA/DM-2,6-NDC mixture contained 40-43% 2,6-NDA and 44-45% by weight DM-2,6-NDC. No esterification catalysts were used.
[b]Used for Runs 1-4.
[c]Used for Runs 5-9.
[d]Agitation rate, 360 cycles/minute.

Samples of 2,6-NDA were esterfied with methanol using a 4:1 weight ratio of methanol to 2,6-NDA, rather than the 8:1 ratio used in Example 1. The results of these esterification reactions are shown in Table 2. The same reactor and procedure was used as described in Example 1. In runs 1-5, the reaction temperature was 530° F., whereas in runs 6-8, the reaction temperature was 600° F.

These data show that the higher reaction temperature of 600° F. converts the 2,6-NDA in 20-25% as much time compared to a reaction temperature of 530° F., does not increase the amount of "other" by-products and, importantly, for a given acid conversion, yields only 70% as much DME.

EXAMPLE 3

The esterification of pure 2,6-naphthalenedicarboxylic acid with methanol was conducted in the same manner as described in Example 2. This pure 2,6-NDA was obtained by the hydrolysis of pure DM-2,6-NDC. The data is shown in Table 3.

Runs 1-5 in Table 3 were conducted at 530° F. These runs demonstrate that 65% of the acid groups were converted in 10 min, and 80% conversion occurred after 20 min. The weight percent DME in the liquid product was 0.3 wt. % after 10 min and 0.54 wt. % after 20 min.

A second set of esterification runs using the same 2,6-NDA were conducted at 600° F. These data are also in Table 3. In these higher temperature runs, 65% conversion of the acid groups was obtained in 5 min. Thus, the esterification reaction was 4-5 times faster at the elevated temperature but, importantly, the amount of "other" impurities generated was less than 0.4% at 80% acid group conversion, which is lower than the value of 0.54% DME formed at the lower temperature.

TABLE 2

| RUN #[a] | 2,6-NDA[b] Feedstock | 1 | 2 | 3 | 4 | 5 | 6 | 7 | 8 | 9 |
|---|---|---|---|---|---|---|---|---|---|---|
| REACTION CONDITIONS[c] | | | | | | | | | | |
| Temperature (°F.) | | 530 | 530 | 530 | 530 | 530 | 600 | 600 | 600 | 600 |
| Residence Time (Minutes) | | 0 | 2 | 5 | 10 | 20 | 0 | 1 | 2 | 5 |
| PRODUCT (OR 2,6-NDA) ANALYSIS | | | | | | | | | | |
| Weight of Product (g) | | 14.0 | 14.0 | 14.1 | 14.1 | 14.1 | 14.1 | 14.1 | 14.2 | 14.1 |
| Weight % of Loss (gain) | | (0.1) | 0.1 | (0.8) | (0.6) | (0.8) | (1.1) | (0.9) | (1.4) | (1.1) |
| Dry Weight (g) | | 5.9 | 5.8 | 5.9 | 5.9 | 6.0 | 5.9 | 6.0 | 6.1 | 6.1 |
| ANALYSIS OF DRY PRODUCT (WT. %) | | | | | | | | | | |
| TMLA | 0.70 | 0.23 | 0.04 | 0.01 | 0.00 | 0.00 | 0.01 | 0.00 | 0.00 | 0.00 |
| 2,6-NDA | 33.47 | 30.48 | 25.41 | 13.96 | 4.75 | 3.13 | 18.52 | 6.84 | 4.42 | 3.05 |
| Br2,6-NDA | 0.19 | 0.18 | 0.13 | 0.07 | 0.01 | 0.00 | 0.10 | 0.04 | 0.00 | 0.00 |
| FNA | 0.12 | 0.11 | 0.08 | 0.05 | 0.02 | 0.01 | 0.07 | 0.03 | 0.02 | 0.00 |
| TMTM | 1.69 | 0.42 | 0.09 | 0.06 | 0.06 | 0.10 | 0.18 | 0.78 | 0.94 | 0.89 |
| 2-NA | 0.01 | 0.01 | 0.00 | 0.00 | 0.00 | 0.01 | 0.00 | 0.00 | 0.01 | 0.00 |
| MM-2,6-NDC | 9.69 | 11.16 | 13.06 | 17.24 | 14.65 | 6.46 | 17.02 | 17.44 | 13.30 | 4.39 |
| MeFNA | 0.20 | 0.12 | 0.10 | 0.10 | 0.10 | 0.11 | 0.12 | 0.17 | 0.19 | 0.16 |
| Me2NA | 0.03 | 0.06 | 0.00 | 0.00 | 0.00 | 0.00 | 0.02 | 0.02 | 0.00 | 0.01 |
| DM-2,6-NDC | 45.83 | 51.13 | 54.74 | 61.41 | 71.62 | 78.47 | 55.95 | 64.23 | 71.57 | 80.51 |
| Br-2,6-NDC | 0.39 | 0.27 | 0.17 | 0.15 | 0.20 | 0.31 | 0.26 | 0.30 | 0.39 | 0.38 |
| Others | 1.95 | 2.18 | 1.92 | 2.07 | 1.43 | 2.10 | 1.83 | 1.52 | 2.08 | 1.42 |
| TOTAL WT. % | 94.27 | 96.35 | 95.73 | 95.14 | 92.85 | 90.70 | 94.09 | 91.38 | 92.92 | 90.82 |
| ANALYSIS OF DRY PRODUCT (Mole %) | | | | | | | | | | |
| 2,6-NDA | 40.3 | 35.4 | 29.5 | 16.5 | 5.8 | 4.0 | 22.1 | 8.5 | 5.5 | 3.9 |
| MM-2,6-NDC | 10.9 | 12.2 | 14.2 | 19.2 | 16.8 | 7.7 | 19.0 | 20.5 | 15.6 | 5.3 |
| DM-2,6-NDC | 48.8 | 52.5 | 56.3 | 64.3 | 77.4 | 88.3 | 58.9 | 71.0 | 78.9 | 90.8 |
| Total Acid Groups | 45.7 | 41.4 | 36.6 | 26.1 | 14.2 | 7.8 | 31.6 | 18.8 | 13.3 | 6.5 |

TABLE 2-continued

| RUN #[a] | 2,6-NDA[b] Feedstock | 1 | 2 | 3 | 4 | 5 | 6 | 7 | 8 | 9 |
|---|---|---|---|---|---|---|---|---|---|---|
| Total Ester Groups | 54.3 | 58.6 | 63.4 | 73.9 | 85.8 | 92.2 | 68.4 | 81.2 | 86.7 | 93.5 |
| METALS ANALYSIS OF FEEDSTOCK (WT. %) | | | | | | | | | | |
| Cobalt | 0.103 | | | | | | | | | |
| Manganese | 0.667 | | | | | | | | | |
| Bromine | 0.306 | | | | | | | | | |
| FILTRATE ANALYSIS | | | | | | | | | | |
| Weight % DME | | 0.09 | 0.23 | 0.51 | 1.03 | 2.00 | 0.23 | 0.42 | 0.71 | 1.14 |
| Weight % H$_2$O | | 2.10 | 1.81 | 4.34 | 4.04 | 7.09 | 3.73 | 4.35 | 4.22 | 5.51 |
| MOLE % ACID GROUP CONVERSION | | 9.4 | 19.9 | 42.9 | 69.0 | 82.9 | 31.0 | 59.0 | 70.9 | 85.7 |

[a]All reactions were conducted using 8.0 g of methanol and 6.0 g 2,6-NDA/DM-2,6-NDC mixture. No esterification catalysts were used.
[b]2,6-NDA/DM-2,6-NDC mixture used for all runs.
[c]Agitation rate was 360 cycles/minute for all runs.

TABLE 3

| RUN #[a] | 2,6-NDA[b] Feedstock | 1 | 2 | 3 | 4 | 5 | 6 | 7 | 8 | 9 |
|---|---|---|---|---|---|---|---|---|---|---|
| REACTION CONDITIONS[c] | | | | | | | | | | |
| Temperature (°F.) | | 530 | 530 | 530 | 530 | 530 | 600 | 600 | 600 | 600 |
| Residence Time (Minutes) | | 0 | 2 | 5 | 10 | 20 | 0 | 1 | 2 | 5 |
| PRODUCT (OR 2,6-NDA) ANALYSIS | | | | | | | | | | |
| Weight of Product (g) | | 14.0 | 14.0 | 14.1 | 14.2 | 14.1 | 14.1 | 14.1 | 14.2 | 14.2 |
| Weight % of Loss (gain) | | 0.2 | (*0.4) | (0.6) | (1.2) | 0.6) | (0.9) | (1.1) | (1.3) | (1.5) |
| Dry Weight (g) | | 6.0 | 5.9 | 6.0 | 6.2 | 6.2 | 6.0 | 6.2 | 6.2 | 6.2 |
| ANALYSIS OF DRY PROUDUCT (WT. %) | | | | | | | | | | |
| 2,6-NDA | 33.30 | 26.83 | 26.54 | 19.10 | 3.44 | 0.82 | 23.88 | 6.35 | 3.10 | 0.78 |
| 2-NA | | 0.0 | 0.0 | 0.0 | 0.0 | 0.0 | 0.0 | 0.0 | 0.0 | 0.0 |
| MM-2,6-NDC | 0.00 | 3.56 | 4.08 | 8.75 | 14.33 | 10.33 | 6.76 | 16.51 | 15.75 | 10.69 |
| Me2NA | | 0.00 | 0.00 | 0.00 | 0.00 | 0.00 | 0.00 | 0.00 | 0.00 | 0.00 |
| DM-2,6-NDC | 66.70 | 62.69 | 62.40 | 64.56 | 73.24 | 78.84 | 62.20 | 69.76 | 73.20 | 78.92 |
| Others | | 0.09 | 0.09 | 0.08 | 0.08 | 0.09 | 0.22 | 0.31 | 0.33 | 0.36 |
| TOTAL WT. % | | 93.17 | 93.12 | 92.49 | 91.09 | 90.06 | 93.06 | 92.94 | 92.38 | 90.76 |
| ANALYSIS OF DRY PRODUCT (MOLE %) | | | | | | | | | | |
| 2,6-NDA | 36.1 | 31.3 | 31.0 | 22.6 | 4.2 | 1.0 | 28.0 | 7.6 | 3.7 | 1.0 |
| MM-2,6-NDC | 0.0 | 3.9 | 4.5 | 9.7 | 16.5 | 12.1 | 7.4 | 18.5 | 17.9 | 12.4 |
| DM-2,6-NDC | 63.9 | 64.8 | 64.5 | 67.7 | 79.3 | 86.9 | 64.6 | 73.9 | 78.4 | 86.6 |
| Total Acid Groups | 36.1 | 33.3 | 33.2 | 27.5 | 12.4 | 7.1 | 31.7 | 16.9 | 12.7 | 7.2 |
| Total Ester Groups | 63.9 | 66.7 | 66.8 | 72.5 | 87.6 | 92.9 | 68.3 | 83.1 | 87.3 | 92.8 |
| METALS ANALYSIS, Co, Mn, Br (Wt. %) | 0.0 | | | | | | | | | |
| FILTRATE ANALYSIS | | | | | | | | | | |
| Weight % DME | | 0.04 | 0.05 | 0.12 | 0.31 | 0.54 | 0.05 | 0.18 | 0.28 | 0.41 |
| Weight % H$_2$O | | 2.72 | 0.60 | 1.50 | 4.01 | 3.62 | 1.23 | 2.12 | 2.76 | 3.16 |
| MOLE % ACID GROUP | | 7.7 | 7.8 | 23.8 | 65.5 | 80.4 | 12.0 | 53.2 | 64.8 | 80.1 |

[a]All reactions were conducted using 8.0 g of methanol and 6.0 g of the 2,6-NDA/DM-2,6-NDC mixture. No esterification catalysts were used.
[b]2,6-NDA/DM-2,6-NDC mixture used for all runs.
[c]Agitation rate was 360 cycles/minute.

EXAMPLE 4

This Example demonstrates that only a portion of the methanol charged to the esterification reaction mixture is in the liquid phase at a reaction temperature of 600° F., the remainder being in the gaseous phase.

A 300 ml pressure reactor was charged with 16 g of pure DM-2,6-NDC and 64 g of methanol (1:4 ratio). A sample dip-tube was inserted through the head of the reactor to a point about ⅛" from the lowest point in the reactor. After purging with helium, the reactor was heated with stirring to 600° F., yielding a pressure of 1980 psig. A sample was taken via the heated sample line into a pressure sample vessel. The amount of sample was about 6.5 g. Stirring was used during heat-up but was stopped before sampling. The closed sample vessel was cooled, weighed, and then completely emptied into a glass dish. After evaporation of methanol from the dish, the weight of the solid was determined.

In three runs, the following values were obtained:

(a) 66.0% (wt.) solids (only a 2.5 g sample obtained due to sample line plugging),
(b) 65.7% (wt.) solids (a normal sample)
(c) 68.6% (wt.) solids (a normal sample)

On the average, the methanol/DM-2,6-NDC ratio in the liquid phase was 0.5:1, compared to a 4:1 ratio in the feed. Thus, approximately only 12.5% of the methanol was in the liquid phase under these conditions, whereas approximately 87.5% was in the vapor phase. Thus, in the reactions described in the previous examples, only a portion of the methanol was in the liquid phase and yet the esterification reaction proceeded rapidly.

EXAMPLE 5

In this Example, 2,6-naphthalenedicarboxylic acid, prepared by the cobalt, manganese, bromine catalyzed oxidation of 2,6-dimethylnaphthalene, was esterified in an esterification reactor essentially the same as that shown in the Figure, except that the temperature of the reaction mixture was maintained by external electric heaters and the entire product was withdrawn through a single exit port located at the top of the uppermost compartment. The total volume of the cylindrical reactor was approximately 0.83 gal with an inner diameter of 3 in. The bottom compartment was 9" high and each of the other compartments were 4.5" high.

A slurry of 20 wt. % 2,6-NDA and 80 wt. % methanol was pumped into the reactor at a rate of 15.8 lbs/hr. It was heated to 484° F. in a tubular preheater prior to entering the reactor. The inside of the reactor was kept at 600° F. by the external electric heaters. The reactor pressure was maintained at 1250 psig.

The agitator speed was 500 rpm. Flush streams of 0.9 lb/hr methanol and 2 standard cubic feet of nitrogen per hour were injected through the magnetic stirrer drive to keep product from entering the stirrer drive. The reactor effluent was cooled to 358° F. in a tubular heat exchanger and passed through a sintered stainless steel filter with nominal and absolute ratings of 0.5 and 5 microns, respectively. The product was collected for 5.25 hr in a stirred receiver heated to 315° F. and pressurized to 250 psig.

The product was crystallized by cooling to about 60° F. The resulting slurry was passed through a pressure filter. Methanol (36.4 lbs.) was pumped into the receiver and through the filter in order to wash the filter cake.

lbs/hr. This methanol was heated to 907° F. in another tubular preheater. The inside of the reactor was kept at an average temperature of about 577° F. by external electric heaters and the reactor pressure was maintained at 1250 psig. The agitator speed was 750 rpm. The agitator flushing and product collection systems were as described in Example 5.

The contents of each compartment were sampled using high-pressure bombs with a volume of about 30 ml each. The first compartment was sampled through the side wall at a point 4.5" above the bottom of the compartment. The other compartments were sampled through the side wall at a point 0.5" above the bottom of the respective compartment. Table 4 shows the internal temperature for each compartment, the total weight for each sample, the weight after the methanol and water (methanol and water comprise most of the volatiles) were removed by drying at 203° F. and 20" Hg vacuum for 5 hr, and analyses of the dried solids by liquid chromatography. As the data demonstrate, there is a steady decrease in 2,6-NDA and MM-2,6-NDC through the fourth compartment. The compositions in the fourth and fifth compartments are nearly equal. These data demonstrate the excellent conversion of 2,6NDA to DM-2,6-NDC provided by the process of this invention.

TABLE 4

| COMPARTMENT NO. | 2,6-NDA[a] FEEDSTOCK | 1 | 2 | 3 | 4 | 5 (Top) |
|---|---|---|---|---|---|---|
| INTERNAL TEMPERATURE (°F.) |  | 571 | 586 | 580 | 579 | 575 |
| WET WEIGHT (g) |  | 25.10 | 25.90 | 25.60 | 26.20 | 26.90 |
| DRY WEIGHT (g) |  | 21.00 | 20.82 | 21.49 | 22.05 | 22.46 |
| WT. % VOLATILES |  | 16.3 | 19.6 | 16.1 | 15.8 | 16.5 |
| ANALYSIS OF DRY PRODUCT (WT. %): |  |  |  |  |  |  |
| TMLA | 0.40 | ND | ND | ND | ND | ND |
| 2,6-NDA | 98.95 | 6.37 | 1.44 | 0.62 | 0.38 | 0.40 |
| Br-2,6-NDA | 0.47 | 0.038 | ND | ND | ND | ND |
| FNA | 0.65 | 0.072 | 0.025 | 0.01 | 0.002 | 0.003 |
| TMTM | ND | 0.27 | 0.23 | 0.24 | 0.17 | 0.25 |
| MM-2,6-NDC | ND | 12.48 | 8.19 | 5.50 | 4.02 | 3.82 |
| MeFNA | ND | 0.41 | 0.40 | 0.40 | 0.34 | 0.39 |
| Me2NA | ND | ND | ND | ND | ND | ND |
| DM-2,6-NDC | ND | 68.31 | 75.61 | 79.74 | 81.29 | 81.33 |
| Br-2,6-NDC | ND | 0.37 | 0.40 | 0.42 | 0.32 | 0.39 |
| XRF, WT. %: |  |  |  |  |  |  |
| Br | 0.8 |  |  |  |  |  |
| Co | 0.047 |  |  |  |  |  |
| Mn | 0.2 |  |  |  |  |  |

[a]2,6-NDA Feedstock used for the esterification reaction.

The filter cake was dried at 105° C. The weight after drying was 14.4 lb. It contained 0.92% monomethyl 2,6-naphthalenedicarboxylate and 0.019% of the methyl ester of 6-formyl-2-naphthoic acid by weight, as determined by liquid chromatography.

This Example demonstrates that the esterification of 2,6-naphthalenedicarboxylic acid with methanol is very efficient when using the process of this invention.

EXAMPLE 6

In this Example, 2,6-naphthalenedicarboxylic acid, prepared by the cobalt, manganese, bromine catalyzed oxidation of 2,6-dimethylnaphthalene, was esterified in the esterification reactor described in Example 5.

A slurry of 19.0% 2,6-NDA, 4.8% DM-2,6-NDC, and 76.2% methanol, by weight, was pumped into the reactor bottom at a rate of 21 lbs/hr. It was heated to 437° F. in a tubular preheater prior to entering the reactor. Simultaneously, methanol was pumped into the reactor bottom through a separate port at a rate of 4

EXAMPLE 7

In this Example, 2,6-naphthalenedicarboxylic acid, prepared by the cobalt, manganese, bromine catalyzed oxidation of 2,6-dimethylnaphthalene, was esterified in the esterification reactor described in Example 5.

A slurry of 19.0% 2,6-NDA, 4.8% DM-2,6-NDC, and 76.2% methanol, by weight, was pumped into the reactor bottom at a rate of 21 lbs/hr. It was heated to 445° F. in a tubular preheater prior to entering the reactor. Simultaneously, methanol was pumped into the reactor bottom through a separate port at a rate of 4 lbs/hr. This methanol was heated to 863° F. in a separate tubular preheater. The inside of the reactor was kept at an average temperature of about 568° F. by external electric heaters and the reactor pressure was maintained at 1250 psig. The agitator speed was 750 rpm. The agitator flushing and product collection systems were as described in Example 5.

The contents of each compartment were sampled, as in Example 6. Table 5 shows the total weight for each example, the weight after the methanol and water had been removed by drying at 203° F. and 20" Hg vacuum for 5 hr, and analyses of the dried solids by liquid chromatography. Compared to Example 6, the 2,6-NDA concentration in the first compartment is considerably higher, and there is a steady decrease in both 2,6-NDA and MM-2,6-NDC all the way through the fifth compartment. The MM-2,6-NDC concentration in the fifth compartment (about 2.5 wt. % on a dry basis) is lower than what can be achieved in a liquid-filled, methanol-rich esterification reactor with the same overall feed composition (20% 2,6-NDA, 80% methanol, by weight). The reason is that in a liquid-filled system all the by-product water stays in the liquid phase, thus limiting the conversion. In the preferred mode of our invention, most of the by-product water goes into the vapor phase, due to its low solubility in the liquid. This effect enables us to obtain a high conversion while operating in the desirable co-current mode.

TABLE 5

| COMPARTMENT NO. | 2,6-NDA[a] FEEDSTOCK | 1 | 2 | 3 | 4 | 5 (Top) |
|---|---|---|---|---|---|---|
| INTERNAL TEMPERATURE (°F.) | | 564 | 577 | 572 | 568 | 564 |
| WET WEIGHT (g) | | 27.10 | 26.00 | 25.80 | 25.70 | 25.60 |
| DRY WEIGHT (g) | | 23.21 | 21.33 | 20.47 | 21.54 | 20.68 |
| WT. % VOLATILES | | 14.4 | 18.0 | 20.7 | 16.2 | 19.2 |
| LC, WT. %: | | | | | | |
| TMLA | 0.40 | ND | ND | ND | ND | ND |
| 2,6-NDA | 98.95 | 17.41 | 2.85 | 1.02 | 0.65 | 0.43 |
| BrNDA | 0.47 | 0.065 | 0.007 | ND | ND | ND |
| FNA | 0.65 | 0.105 | 0.029 | 0.011 | 0.006 | 0.004 |
| TMTM | ND | 0.10 | 0.20 | 0.18 | 0.15 | 0.12 |
| MM-2,6-NDC | ND | 10.86 | 8.43 | 5.34 | 3.34 | 2.48 |
| MeFNE | ND | 0.35 | 0.42 | 0.38 | 0.38 | 0.32 |
| Me2NA | ND | ND | ND | ND | ND | ND |
| DM-2,6-NDC | ND | 59.08 | 71.70 | 76.42 | 78.34 | 79.09 |
| Br-2,6-NDC | ND | 0.38 | 0.53 | 0.43 | 0.50 | 0.42 |
| XRF, WT. %: | | | | | | |
| Br | 0.28 | | | | | |
| Co | 0.047 | | | | | |
| Mn | 0.2 | | | | | |

[a] 2,6-NDA feedstock used for the esterification reaction.

These examples demonstrate the advantages that are obtained by using the process of the present invention for the esterification of a naphthalenedicarboxylic acid. While the process of the present invention has been illustrated and described with reference to several preferred embodiments, the present invention is not limited thereto. Alternatives, changes and modifications are possible and will become apparent to those skilled in the art upon reference to the foregoing description and the drawing. Accordingly, such alternatives, changes and modifications form a part of the invention insofar as they fall within the spirit and scope of the appended claims.

Having described the invention, that which is claimed is:

1. A continuous process for preparing a dialkylester of a naphthalenedicarboxylic acid comprising passing a liquid phase reaction mixture comprising a low molecular weight alcohol, a naphthalenedicarboxylic acid and a dialkylester of a naphthalenedicarboxylic acid at a temperature in the range of about 500° F. to about 700° F. and at a pressure in the range of about 5 to about 250 atmospheres absolute through series arranged reaction zones while introducing a naphthalenedicarboxylic acid and a low molecular weight alcohol to an upstream reaction zone, agitating at least one reaction zone, and removing a product comprising a dialkylester formed by the reaction of the naphthalenedicarboxylic acid with the low molecular weight alcohol from a downstream reaction zone.

2. The process of claim 1 wherein there are about 2 to about 20 reaction zones.

3. The process of claim 2 wherein the low molecular weight alcohol is methanol, the naphthalenedicarboxylic acid is 2,6-naphthelendicarboxylic acid and the dialkylester produced is dimethyl-2,6-naphthalenedicarboxylate.

4. The process of claim 1 wherein most of the alcohol added to the series arranged reaction zones is present in the reaction zones in the gas phase.

5. The process of claim 1 wherein each reaction zone is equipped with an agitator to agitate the liquid phase reaction mixture present in the reaction zone.

6. The process of claim 1 wherein the reaction zones are stirred tank reactors.

7. A process for preparing a dialkylester of a naphthalenedicarboxylic acid comprising contacting a low molecular weight alcohol and a naphthalenedicarboxylic acid in a liquid esterification reaction mixture comprising a dialkylester of the naphthalenedicarboxylic acid, at a temperature in the range of about 500° F. to about 700° F. and at a pressure in the range of about 5 to about 250 atmospheres absolute in a vertically arranged, compartmented reactor having at least an upper and lower compartment, the compartments being separated by a dividing means having an opening to permit the upward flow of the esterification reaction mixture between reactor compartments, and where the low molecular weight alcohol and the naphthalenedicarboxylic acid are added to a lower compartment or compartments, and a reaction product mixture comprising a diester of naphthalenedicarboxylic acid is removed from an upper reactor compartment.

8. The process of claim 7 wherein the compartmented reactor comprises about 3 to about 8 compartments.

9. The process of claim 8 wherein all of the compartments are equipped with an agitator to agitate the liquid reaction mixture present in the compartment.

10. The process of claim 7 wherein the low molecular weight alcohol is methanol, the naphthalenedicarboxylic acid is 2,6-naphthalenedicarboxylic acid and the product mixture comprises dimethyl-2,6-naphthalenedicarboxylate.

11. The process of claim 7 wherein at least a portion of the alcohol added to the compartmented reactor passes through the compartmented reactor as gaseous alcohol.

12. The process of claim 11 wherein most of the alcohol added to the compartmented reactor is in the liquid phase and in the form of a slurry with the naphthalenedicarboxylic acid.

13. The process of claim 10 wherein the compartmented reactor comprises about 2 to about 20 compartments.

14. The process of claim 13 wherein most of the methanol added to the compartmented reactor passes through the reactor in the gaseous state.

15. The process of claim 14 wherein the esterification reaction temperature is in the range of about 540° F. to about 660° F. and the pressure is about 20 atmospheres absolute to about 150 atmospheres absolute.

16. The process of claim 14 wherein the weight ratio of methanol to 2,6-naphthalenedicarboxylic acid added to the compartmented reactor is in the range of about 1:1 to about 10:1.

17. The process of claim 16 wherein most of the methanol and most of the 2,6-naphthalenedicarboxylic acid added to the compartmented reactor is in the form of a slurry of the 2,6-naphthalenedicarboxylic acid in liquid methanol.

18. A process for preparing a diester of a naphthalenedicarboxylic acid comprising contacting the naphthalenedicarboxylic acid with a low molecular weight alcohol in a suitable reaction zone and in a reaction mixture comprising a liquid dialkylester of a naphthalenedicarboxylic acid, a naphthalenedicarboxylic acid and a low molecular weight alcohol, under reaction conditions where the low molecular weight alcohol is present in the reaction mixture in both the liquid and the gas phase, where low molecular weight alcohol is added to the reaction zone and simultaneously removed from the reaction zone such that the ratio of the rate of removal of the alcohol in pounds per hour from the reaction zone in the gas phase to the rate of addition of the alcohol to the reaction zone in pounds per hour is about 0.5:1 to about 0.99:1.

19. The process of claim 18 wherein the alcohol is methanol, the naphthalenedicarboxylic acid is 2,6-naphthalenedicarboxylic acid and the liquid dialkylester of a naphthalenedicarboxylic acid is dimethyl-2,6-naphthalenedicarboxylate.

* * * * *

UNITED STATES PATENT AND TRADEMARK OFFICE
CERTIFICATE OF CORRECTION

PATENT NO. : 5,350,874
DATED : September 27, 1994
INVENTOR(S) : Paul K. Behrens, Juergen K. Holzhauer, Gregory P. Hussmann, David L. Sikkenga It is certified that error appears in the above-indentified patent and that said Letters Patent is hereby corrected as shown below:

| Col. | Line | |
|---|---|---|
| 3 | 18 | "convened to a diaikylether," should read --converted to a dialkylether,-- |
| 5 | 29 | "aidehyde" should read --aldehyde-- |
| 8 | 46 | "pan of the total alcohol" should read --part of the total alcohol-- |
| 8 | 59-60 | "The naphthalenedicarboxytic acid" should read --The naphthalenedicarboxylic acid-- |
| 16 | 55 | in Table 2, in the line "2,6-NDA" and in the column "3" patent reads "13.96" patent should read --13.98-- |

Signed and Sealed this

Thirteenth Day of February, 1996

Attest:

BRUCE LEHMAN

Attesting Officer  Commissioner of Patents and Trademarks